US008834852B2

(12) United States Patent
Itano et al.

(10) Patent No.: US 8,834,852 B2
(45) Date of Patent: Sep. 16, 2014

(54) COMPOSITION FOR ORAL CAVITY

(75) Inventors: Morihide Itano, Tokyo (JP); Shigeto Kayane, Tokyo (JP); Katsuya Ueno, Wakayama (JP); Hiromoto Mizushima, Wakayama (JP)

(73) Assignee: Kao Corporation, Tokyo (JP)

( * ) Notice: Subject to any disclaimer, the term of this patent is extended or adjusted under 35 U.S.C. 154(b) by 370 days.

(21) Appl. No.: 12/772,492

(22) Filed: May 3, 2010

(65) Prior Publication Data
US 2010/0215592 A1 Aug. 26, 2010

Related U.S. Application Data

(62) Division of application No. 11/576,114, filed as application No. PCT/JP2005/017863 on Sep. 28, 2005, now abandoned.

(30) Foreign Application Priority Data

Sep. 29, 2004 (JP) ................................. 2004-283407

(51) Int. Cl.
*A61K 8/00* (2006.01)
*A61K 8/18* (2006.01)
*A61Q 11/00* (2006.01)
*A01N 43/04* (2006.01)
*A61K 31/70* (2006.01)
*A61Q 17/00* (2006.01)
*A61K 8/60* (2006.01)
*A61K 8/34* (2006.01)
*A61K 8/39* (2006.01)
*A61K 8/73* (2006.01)
*A61K 31/7028* (2006.01)
*A61K 31/7032* (2006.01)

(52) U.S. Cl.
CPC .............. *A61Q 17/005* (2013.01); *A61K 8/608* (2013.01); *A61K 8/34* (2013.01); *A61K 8/39* (2013.01); *A61K 8/602* (2013.01); *A61K 8/604* (2013.01); *A61K 8/73* (2013.01); *A61K 31/7028* (2013.01); *A61K 31/7032* (2013.01); *A61Q 11/00* (2013.01)
USPC .............................................. 424/49; 514/25

(58) Field of Classification Search
CPC ........... A61K 8/34; A61K 8/39; A61K 8/602; A61K 8/604; A61K 8/608; A61K 31/7032; A61K 31/7028; A61Q 11/00; A61Q 17/005
USPC .............................................. 424/49; 514/25
See application file for complete search history.

(56) References Cited

U.S. PATENT DOCUMENTS

| 3,970,747 | A | * | 7/1976 | Barth ............................... 424/52 |
| 4,565,647 | A | | 1/1986 | Llenado |
| 5,409,902 | A | | 4/1995 | Carson et al. |
| 6,165,442 | A | | 12/2000 | Swaerd-Nordmo et al. |
| 6,579,698 | B1 | | 6/2003 | Correa et al. |
| 6,734,155 | B1 | | 5/2004 | Herbots et al. |
| 2003/0175219 | A1 | * | 9/2003 | Francois ........................ 424/49 |
| 2009/0156511 | A1 | | 6/2009 | Ueno et al. |

FOREIGN PATENT DOCUMENTS

| EP | 0 551 674 A1 | 7/1993 |
| JP | B-58-11924 | 3/1983 |
| JP | 2-17120 A | 1/1990 |
| JP | 9-315950 A | 12/1997 |
| JP | 2000-159675 A | 6/2000 |
| JP | A-2002-27975 | 1/2002 |

OTHER PUBLICATIONS

Machine translation of JP09-315950. Published Dec. 1997. Retrieved from the internet on Mar. 12, 2009 at <http://dossier1.ipdl.inpit.go.jp/AIPN/odse_top_dn.ipd?N0000=7400>.*
Rams, T.E., Feik, D., Slots, J. (1990) *Staphylococci* in human periodontal diseases. Oral Microbiology and Immunology, vol. 5, p. 29-32.*
International Search Report for International Application No. PCT/JP2005/017863, Japanese Patent Office, mailed Dec. 27, 2005.
Patent Abstracts of Japan, English abstract of Publication No. JP 09-315950 A, Thickening Gelatin Agent and Cosmetic Containing the Same, published Dec. 9, 1997 (listed on accompanying PTO/Sb/08A as document FP1).
Patent Abstracts of Japan, English abstract of Publication No. JP 02-017120 A, Preventive for Dental Caries, published Jan. 22, 1990 (listed on accompanying PTO/SB/08A as document FP2).

(Continued)

*Primary Examiner* — Scarlett Goon
(74) *Attorney, Agent, or Firm* — Sterne, Kessler, Goldstein & Fox P.L.L.C.

(57) ABSTRACT

The present invention relates to an oral care composition, which contains a compound represented by the formula (A):

[Chemical formula 1]

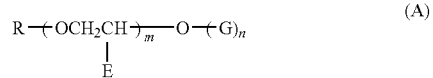

(wherein, R represents a substituted or unsubstituted, linear or branched alkyl group having from 6 to 18 carbon atoms, G represents a galactose residue, m stands for an integer of from 0 to 200, and n stands for an integer of from 1 to 30); and a coaggregation inhibitor of bacteria of the genus *Fusobacterium* and cariogenic bacteria, which contains the compound as an effective ingredient. The composition for oral cavity according to the present invention inhibits coaggregation of bacteria of the genus *Fusobacterium* with cariogenic bacteria so that it has an excellent caries preventive effect.

20 Claims, 2 Drawing Sheets

(56) References Cited

OTHER PUBLICATIONS

Patent Abstracts of Japan, English abstract of Publication No. 2000-159675 A, Antimicrobial Agent, published Jun. 13, 2000 (listed on accompanying PTO/SB/08A as document FP3).

Extended European Search Report for corresponding EPO application No. 05787958.7, mailed Feb. 6, 2009 from the European Patent Office, Munich, Germany.

Kobayashi, T. et al., "Synthesis of alkyl glycosides through β-glucosidase-catalyzed condensation in an aqueous-organic byphasic system and estimation of the equilibrium constants for their formation," *J. Molecular Catalysis B: Enzymatic 11*:13-21 (Nov. 2000), Elsevier Science, Amsterdam, The Netherlands.

Matsumura, S. et al., "Surface activities, biodegradability and antimicrobial properties of n-alkyl glucosides, mannosides and galactosides," *J. American Oil Chemists' Society 67*:996-1001 (Dec. 1990), Springer, Berlin, Germany.

Office Action dated Jun. 2, 2009, for the corresponding EPO application, EP Application No. 05 787 958.7—2108, European Patent Office, Munich, Germany.

Dialog File No. 351, Accession No. 1942637, Derwent World Patents Index English language abstract and patent family for JP-B-58-11924 (JP1983011924 B), published Mar. 5, 1983.

Dialog File No. 351, Accession No. 13693631, Derwent World Patents Index English language abstract and patent family for JP 2002-27975 A, published Jan. 29, 2002.

Takemoto, T, et al., "Characteristics of multimodal co-aggregation between *Fusobacterium nucleatum* and *streptococci*," J Periodontal Res 30(4): 252-7 (Jul. 1995), Munksgaard, Denmark.

Hori, R. et al., "Studies on Carbohydrate Derivatives. V. Syntheses of Alkyl Galactosides and Alkyl Glucosides," Yakugaku Zasshi (J. Pharmaceutical Society of Japan) 79: 80-83 (1958), Pharmaceutical Society of Japan, Tokyo, Japan.

Kolenbrander, Pe et al., "Coaggregation of *Fusobacterium nucleatum, Selenomonas flueggei, Selenomonas infelix, Selenomonas noxia*, and *Selenomonas sputigena* with strains from 11 genera of oral bacteria," Infect Immum 57: 3194-3203 (Oct. 1989), Am. Soc. Microbiology, Washington, DC.

Kroschwitz, J.I., et al., eds., "Sugar Alcohols," in Encyclopedia of Chemical Technology, Fourth Edition, vol. 23, (1997), pp. 92-113, John Wiley & Sons, New York.

Bendas, G. et al., "Synthetic glycolipids as membrane-bound cryoprotectants in the freeze-drying process of liposomes," *Eur. J. Pharm. Sci. 4*:211-222 (Mar. 1996), Elsevier.

"Fungal Infection," from the Pennsylvania State University Milton S. Hershey Medical Center, College of Medicine [online], retrieved from the internet Jun. 25, 2009 from <http://web.archive.org/web/20309 18022156/http://www.hmc.psu.edu/healthinfo/f/fungalinfection.htm>.

Kolenbrander, Pe et al., "Adhere today, here tomorrow: oral bacterial adherence," J. Bacteriol., Jun. 1993; 175: 3247-3252, American Society for Microbiology, Washington, DC.

\* cited by examiner

COMPOSITION FOR ORAL CAVITY

FIELD OF THE INVENTION

The present invention relates to an oral care composition having an excellent anticarious effect and a preventive agent for the coaggregation of the genus *Fusobacterium* and cariogenic bacteria.

BACKGROUND OF THE INVENTION

In a way, dental decay is seen as an oral infectious disease which occurs as a result of adhesion and colonization of pathogenic bacteria to the tooth surface. Oral bacteria colonize the tooth surface according to the following mechanism. First, initial colonization bacteria such as *Streptococcus oralis, Streptococcus sanguis, Streptococcus gordornii* and *Actinomyces naeslundii* adsorb on the surface of enamel covered with a thin film (pellicle) of the saliva. Proliferation of these initial colonization bacteria comes along with their coaggregation, and then starts to form dental plaque. Once the dental plaque has matured, microflora undergoes its transition from facultative anaerobes to obligate anaerobes, and obligate anaerobes, typically such as *Fusobacterium nucleatum*, coaggregate with initial colonization bacteria. Subsequently, coaggregation of *Fusobacterium nucleatum* with periodontal pathogens such as *Actinobacillus actinomycetemcomitans, Porphyromonas gingivalis* and *Prevotella intermedia* ensues, and eventually come to colonize on the tooth surface. Takemoto et al. suggested that *Streptococcus mutans* and *Streptococcus sobrinus*, which are bacteria related to dental decay, coaggregate with *Fusobacterium nucleatum* and therefore have a similar colonization mechanism (Non-patent Document 1).

Such coaggregation is caused by lectin•receptor interaction between bacteria, non-specific electrostatic interaction, adhesive action due to sticky polysaccharide synthesis, or non-specific hydrophobic interaction. The oral bacteria forming the plaque are different from the intestinal bacteria or skin indigenous bacteria and are composed of a flora which peculiarly resides in the oral cavity so that lectin•receptor interaction is thought to play a particularly important role in the colonization of the tooth surface by pathogenic bacteria. The "lectin•receptor interaction" is a stereospecific interaction between adhesin, which is a protein bound to the surface layer of bacteria, and a receptor structure on the surface layer of another bacteria. Most of the lectin•receptor interaction develops hydrocarbon-specific binding.

A lactose sensitive adhesin is a common lectin present in the plaque forming bacteria and it specifically recognizes β-galactoside in lactose. Lactose sensitive adhesin is present widely in the oral bacteria and it is involved in the coaggregation of the genera *Actinomyces, Streptococcus, Porphyromonas, Prevotella, Fusobacterium, Haemophilus, Capnocytophaga, Veillonella, Neisseria* and *Selenomonas* (Non-patent Document 2).

Inhibition of the tooth surface from the colonization by pathogenic bacteria is thought to be effective as preventive means of oral infectious diseases. There are, for example, reports on the use of galactose or lactose to prevent adhesion of plaque to teeth (Patent Document 1) and use of a fatty acid sugar ester in which at least one antibacterial fatty acid having from 10 to 16 carbon atoms has formed an ester linkage with fructose or galactose (Patent Document 2).
[Patent Document 1] JP-B-S58-11924
[Patent Document 2] JP-A-2000-159675

[Non-patent Document 1] Journal of Periodontal Research, Vol. 30, p 252-257
[Non-patent Document 2] Infection and Immunity, Vol. 57, p 3194-3203

DISCLOSURE OF THE INVENTION

In the present invention, there is provided an oral care composition, which contains a compound represented by the following formula (A):

[Chemical formula 1]

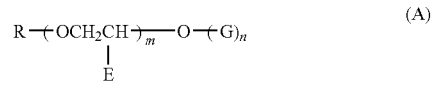

(A)

(wherein, R represents a substituted or unsubstituted, linear or branched alkyl group having from 6 to 18 carbon atoms, G represents a galactose residue, E represents a hydrogen atom or a methyl group, m stands for an integer of from 0 to 200, and n stands for an integer of from 1 to 30).

In the present invention, there is also provided an oral care composition, which contains a compound represented by the following formula (C):

[Chemical formula 2]

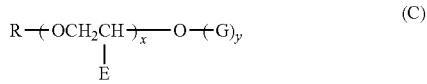

(C)

(wherein, R represents a substituted or unsubstituted, linear or branched alkyl group having from 6 to 18 carbon atoms on average, G represents a galactose residue, E represents a hydrogen atom or a methyl group, x stands for the number of from 0 to 200 and y stands for the number of from 1 to 30).

MODE FOR CARRYING OUT THE INVENTION

Figure 1:
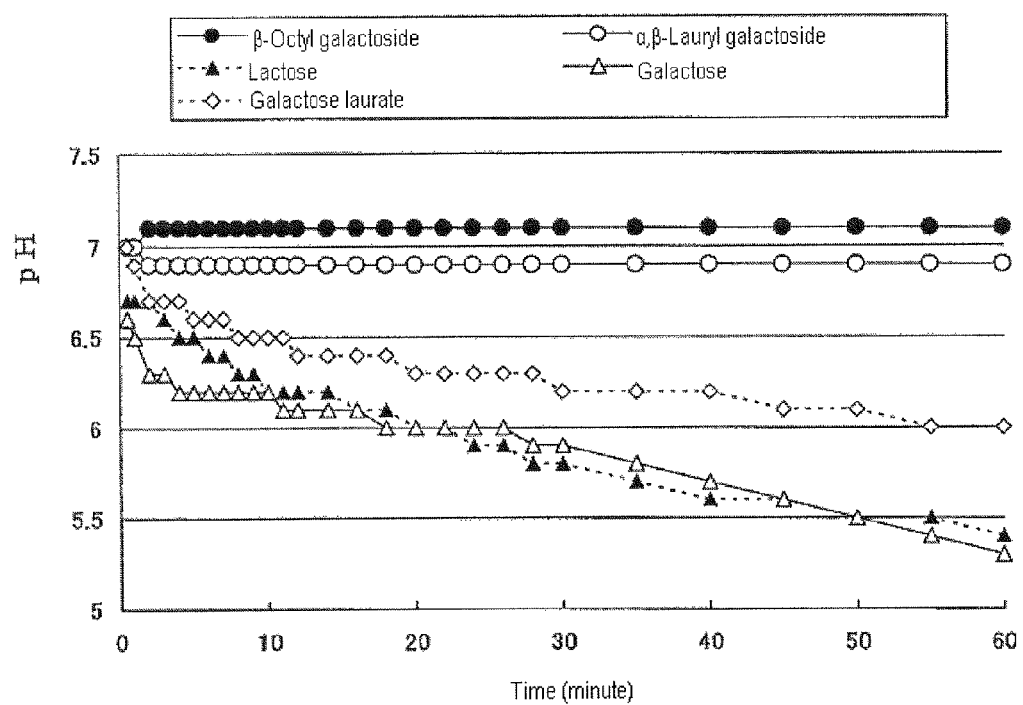
FIG. 1 illustrates a pH change in oral cavity after application thereto of a mouth wash.

Galactose or lactose as described in Patent Document 1 is not preferred because bacteria in the oral cavity convert it into an acid which will cause caries. A fatty acid sugar ester as described in Patent Document 2 also has a similar problem that it generates fructose or galactose, catalizing by the component of the oral care composition or by the hydrolysis in the oral cavity.

The present invention provides therefore, at a low cost, an oral care composition containing a component exhibiting a potent coaggregation inhibition effect against cariogenic bacteria, preventing the formation of plaque, and not generating an acid in the oral cavity.

The present inventors have carried out investigation on various components on the inhibition against the coaggregation of bacteria of the genus *Fusobacterium* with cariogenic bacteria and the generation of an acid in the oral cavity. As a result, it has been found that a compound represented by the formula (A) has a strong coaggregation-inhibiting effect and generates no acid by the oral bacteria so that an oral care composition useful for preventing dental caries is obtainable by the incorporation of it therein.

When the composition of the present invention is used, generation of an acid can be minimized and owing to the coaggregation-inhibiting effect, the cariogenic bacteria in plaque can be reduced. This results in weakening of the plaque and easy plaque control, which makes it possible to prevent tooth decay and the like.

The compound of the formula (A) to be used in the present invention is a compound in which at least one galactose residue forms an ether linkage in the α-configuration or β-configuration with an alkyl group having from 6 to 18 carbon atoms directly or via at least one oxyethylene group or oxypropylene group. The alkyl group may be either linear or branched. Examples include n-hexyl, n-heptyl, n-octyl, n-decyl, n-dodecyl, n-tetradecyl, n-hexadecyl, n-octadecyl, isostearyl (isooctadecyl), and 2-ethylhexyl. From the viewpoints of taste, retention in the oral cavity and foaming property, alkyl groups having from 8 to 16 carbon atoms are preferred, those having from 10 to 14 carbon atoms are more preferred, and among them, a lauryl group is preferred. At least one hydrogen atom of the alkyl group may be substituted with a substituent. Examples of the substituent include alkoxy groups having from 1 to 6 carbon atoms, halogen atoms (such as fluorine, chlorine, bromine and iodine), nitro group, haloalkyl groups having from 1 to 6 carbon atoms, and haloalkoxy groups having from 1 to 6 carbon atoms. The galactose of the compound of the formula (A) to be used in the present invention embraces any of that in pyranose form, furanose form, or mixed form thereof. In the formula (A), m stands for an integer of from 0 to 200, but it is preferably from 0 to 12, more preferably from 0 to 3 from the viewpoint of the coaggregation inhibition effect. The n which represents the condensation degree of galactose is an integer of from 1 to 30, but it is preferably from 1 to 6, more preferably from 1 to 3 from the viewpoint of foaming property.

The compound to be used in the invention is preferably a compound of the formula (A) in which E represents a hydrogen atom, that is, a compound represented by the following formula (B):

[Chemical formula 3]

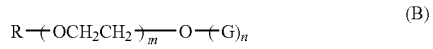

(B)

(wherein, R represents a substituted or unsubstituted, linear or branched alkyl group having from 6 to 18 carbon atoms, G represents a galactose residue, m stands for an integer of from 0 to 200, and n stands for an integer of from 1 to 30).

The compound to be used in the present invention may be a mixture of two or more compounds. In the formula (C), which means a mixture of two or more compounds, the substituted or unsubstituted alkyl group as R is an alkyl group having from 6 to 18 carbon atoms on average. From the standpoints of taste, retention in the oral cavity and foaming property, it is more preferably an alkyl group having from 8 to 16 carbon atoms on average, more preferably from 10 to 14 carbon atoms on average. The average polymerization degree x is from 0 to 200, preferably from 0 to 12, more preferably from 0 to 3. The average condensation degree y of galactose is from 1 to 30, but it is preferably from 1 to 6, more preferably from 1 to 3 from the viewpoint of the coaggregation inhibition effect. The average condensation degree y of galactose can be calculated based on the composition of components having respective condensation degrees determined by the analysis method such as gel permeation chromatography. For example, in the case of an alkyl galactoside mixture in which the condensation degrees of galactose are from 1 to z, the average condensation degree of galactose is represented by the following equation: $y = a_1 \times 1 + a_2 \times 2 + \ldots + a_z \times z = \Sigma(a_z \times z)$ supposing that the molar ratio of the galactoside having a condensation degree of z is $a_z$ ($a_1 + a_2 + a_3 + \ldots a_z = 1$).

The average polymerization degree x of the oxyethylene group or oxypropylene group or average number of carbon atoms of the alkyl group represented by R can be calculated similarly.

Compounds represented by the formulas (A) to (C) can be prepared by the method of Hori et al. (*YAKUGAKU ZASSHI*, Vol. 79, No. 1, p 80-83) or Referential Examples 1 to 3 which will be described later.

Compounds represented by the formula (A) to (C) can strongly inhibit the coaggregation of bacteria of the genus *Fusobacterium* with cariogenic bacteria which are indigenous bacteria. Examples of the bacteria of the genus *Fusobacterium* include *Fusobacterium nucleatum* and *Fusobacterium russii*, while examples of the cariogenic bacteria include *Streptococcus mutans* and *Streptococcus sobrinus*.

Although conventionally known fatty acid sugar esters are decomposed in the oral cavity and generate an acid which will cause dental caries, the compounds of the formulas (A) to (C) to be used in the present invention are not decomposed in the oral cavity as shown in Example 3, which will be described later, and therefore do not generate an acid which will cause dental caries.

The content of any one of the compounds represented by the formulas (A) to (C) in the whole composition of the oral care composition according to the present invention is preferably from 0.05 to 20 mass %, more preferably from 0.1 to 10 mass %, even more preferably from 0.2 to 5 mass %.

According to the investigation by the present inventors, it has been found that sugar alcohols having from 4 to 12 carbon atoms have an action of retarding the binding of bacteria of the genus *Fusobacterium* to cariogenic bacteria and at the same time, do not generate an acid in the oral cavity. This means that these sugar alcohols are also useful as a coaggregation inhibitor. The oral care composition according to the present invention therefore preferably contains a sugar alcohol having from 4 to 12 carbon atoms as an adjuvant of a coaggregation inhibition. Examples of the sugar alcohol having from 4 to 12 carbon atoms include sorbitol, mannitol, xylitol, erythritol, palatinit, and lactitol. The content of the sugar alcohol having from 4 to 12 carbon atoms in the whole composition of the oral care composition according to the present invention is preferably from 4 to 60 mass %, more preferably from 10 to 50 mass %.

Use of the compound represented by any one of the formulas (A) to (C) and the sugar alcohol having from 4 to 12 carbon atoms in combination is also useful from the standpoint of the taste of the composition. The sugar alcohol having from 4 to 12 carbon atoms is added preferably in an amount of from 1 to 500 parts by mass to 1 part by mass of any one of the compounds (A) to (C). In particular, when the composition is a dental paste, the sugar alcohol is preferably added in an amount of from 5 to 400 parts by mass, and when the composition is a mouth wash, the sugar alcohol is preferably added in an amount of from 10 to 200 parts by mass.

The oral care composition according to the present invention may contain, in addition to the above-described essential components, various components, depending on the usage form. For example, components such as humectant, binder, tooth structure reinforcing agent, bactericide, pH regulator, enzyme, anti-inflammatory agent, blood circulation improver, sweetener, antiseptic, colorant, pigment, and flavor can be added as needed. Moreover, surfactants other than the compounds represented by the formulas (A) to (C) may be added insofar as they do not impair the advantage of the present invention.

The oral care composition according to the present invention contains the compound represented by any one of the formulas (A) to (C) and it can be prepared in a conventional manner. It can be provided as cleaning pastes such as powder dentifrice, liquid dentifrice, dental paste, tooth wet powder, and oral pasta; cleaning liquids such as mouth wash, gargling tablets, gingival massage cream, and foods such as chewing gum, troches, and candies.

EXAMPLES

Referential Example 1

Preparation of α,β-lauryl galactoside

D-galactose and lauryl alcohol were reacted in the presence of a catalytic amount of para-toluenesulfonic acid monohydrate while dehydrating under heating and reduced pressure. The mixture thus obtained was purified by a silica gel column into lauryl galactoside having a galactose condensation degree of from 1 to 3. As a result of gel permeation chromatography, gas chromatography and $^1$H-NMR analysis, it has been found that galactose of the resulting lauryl galactoside has an average condensation degree of 1.48; lauryl monogalactoside therein was composed of pyranoside and furanoside at a ratio of 83/17; and an α/β ratio of the pyranoside was 75/25. This lauryl galactoside was provided as α,β-lauryl galactoside as a test substance of Examples 1 to 6.

Referential Example 2

Preparation of β-trioxyethylene lauryl galactoside

Pentaacetyl-D-galactose and trioxyethylene monolauryl ether were reacted at room temperature in dichloromethane in the presence of a boron trifluoride-diethyl ether complex. After the solvent was distilled off under reduced pressure, the residue was purified by a silica gel column into β-trioxyethylene lauryl 2,3,4,6-tetraacetylgalactoside. The resulting product was de-acetylated with sodium methoxide, whereby β-trioxyethylene lauryl galactoside was obtained. $^1$H-NMR (400 MHz, CDCl$_3$) 0.88 (t, 3H), 1.2-1.35 (m, 18H), 1.57 (m, 2H), 3.35-3.8 (overlapped, 13H), 3.84 (t, 2H), 3.97-4.07 (overlapped, 3H), 4.17 (d, 1H), 4.29 (d, J=7.6 Hz, 1H), 4.41 (d, 1H). The resulting product was provided as β-trioxyethylene lauryl galactoside (galactose condensation degree: 1) as a test substance of Example 1.

Referential Example 3

Preparation of α- and β-octyl galactosides

The α,β-octyl galactoside prepared in a similar manner to Referential Example 2 by using octyl alcohol as a raw material was purified by a column into α-octyl galactoside and β-octyl galactoside.
α form: 0.78 (t, 3H), 1.1-1.3 (m, 10H), 1.47 (m, 2H), 3.45-3.70 (overlapped, 7H), 4.63 (d, J=2.8 Hz, 1H), β form: 0.86 (t, 3H), 1.2-1.35 (m, 10H), 1.51 (m, 2H), 3.25-3.75 (overlapped, 7H), 4.09 (d, J=7.6 Hz, 1H). The resulting products were provided as α-octyl galactoside and β-octyl galactoside (each, galactose condensation degree: 1) as a test substance of Examples 1 to 7.

Example 1

Coaggregation Inhibition Effect (1) Strain Used for the Test

Streptococcus sobrinus B13 was used as cariogenic bacteria, while Fusobacterium nucleatum ssp. polymorphum ATCC10953 was used as bacteria of the genus Fusobacterium.

(2) Coaggregation Measurement Method

After inoculation of Streptococcus sobrinus into a brain heart infusion broth, it was cultured at 37° C. for 24 hours under an anaerobic condition. Fusobacterium nucleatum ssp. polymorphum was, on the other hand, inoculated into a GAM bouillon medium and then cultured at 37° C. for 48 hours under an anaerobic condition. After completion of the cultivation, bacteria were collected by centrifugal separation and washed twice with a coaggregation buffer (1 mM tris(hydroxymethyl)aminomethane, 0.1 mM calcium chloride, 0.1 mM magnesium chloride, and 0.15 M sodium chloride). After washing, Fusobacterium nucleatum and Streptococcus sobrinus were adjusted with the coaggregation buffer to give a turbidity (OD: UV-1600, UV-Visible spectrophotometer (product of Shimadzu Corporation)), at wavelength of 600 nm, of 2.0, whereby bacteria suspensions were prepared. Test substances such as a compound represented by the formula (A) were adjusted in advance with the coaggregation buffer to give a concentration of 2% (wt/vol %). Galactose laurate was synthesized in a known manner (Patent Document 2: JP-A-2000-159675). As the other test substances, lactose, galactose, sucrose, glucose, and fructose (each, product of Wako Pure Chemicals), and β-lauryl glucoside, β-lauryl maltoside and sucrose monolaurate (each, product of Dojindo Laboratories) were employed. In the coaggregation test, 400 μL of the suspension of Fusobacterium nucleatum, 200 μL of the suspension of Streptococcus sobrinus, and 200 μL of the 2% (wt/vol %) solution of the test substance were mixed successively by using a No. 2 RIA tube (product of Asahi Techno Glass). After mixing, the mixture was allowed to stand at room temperature for 30 minutes and the mixture in which no precipitation of a clump was observed was evaluated that test substance had a coaggregation inhibition effect (+), while the mixture in which precipitation was observed was evaluated that the test substance had no coaggregation inhibition effect (−).

TABLE 1

| Test substance | Coaggregation inhibition effect |
| --- | --- |
| Test-substance-free group | − |
| α-Octyl galactoside | + |
| β-octyl galactoside | + |
| α,β-lauryl galactoside | + |
| β-Trioxyethylene dodecylgalactoside | + |
| Lactose | + |
| Galactose | + |
| Sucrose | − |
| Glucose | − |
| Fructose | − |
| β-Lauryl glucoside | − |
| β-Lauryl maltoside | − |
| Sucrose monolaurate | − |
| Galactose monolaurate | + |

(3) Results

As shown in Table 1, obvious precipitation due to coaggregation is observed in the control group (test-substance-free group) and sucrose, glucose, fructose, β-lauryl glucoside, β-lauryl maltoside, and sucrose monolaurate. In α-octyl galactoside, β-octyl galactoside, α,β-lauryl galactoside and β-trioxyethylene lauryl galactoside, similarly to lactose, galactose, and galactose laurate, no precipitation due to coaggregation is observed, which has revealed that they have coaggregation inhibition activity.

Example 2

Coaggregation Inhibition Effect (1) Strain to be Used for the Test

*Streptococcus sobrinus* B13 was used as cariogenic bacteria, while *Fusobacterium nucleatum* ssp. *polymorphum* ATCC10953 was used as bacteria of the genus *Fusobacterium*.

(2) Cultivation and Washing

The cariogenic bacteria and bacteria of the genus *Fusobacterium* were cultured on a brain heart infusion broth (product of Becton, Dickinson and Company) and a GAM broth (product of Nissui Pharmaceutical), respectively, under the conditions of 37° C., and 10% $CO_2$, 10% $H_2$, and 80% $N_2$ during from the logarithmic phase to stationary phase. The respective bacteria were collected by centrifugal separation at 5,000 rpm for 5 minutes. After centrifugal washing (for 5 minutes at 5,000 rpm) three times with a coaggregation buffer (1 mM tris(hydroxymethyl)aminomethane, 0.1 mM calcium chloride, 0.1 mM magnesium chloride, and 0.15 M sodium chloride), they were each adjusted to have a turbidity OD at 600 nm of 2.0.

(3) Coaggregation Measurement Method

After addition of 60 μL of each of mannitol, palatinit, erythritol, xylitol, sorbitol and lactitol (product of Wako Pure Chemicals) to a 96-well microtiterplate to give the final concentration of 10% (wt/vol %), 30 μL of the bacteria of the genus *Fusobacterium* was dispensed and stirred, followed by the addition of 30 μL of the cariogenic bacteria. Then, by using a microplate reader (product of Molecular Devices), the turbidity (OD at 600 nm) was measured at one-minute intervals for 30 minutes and a change ratio Vmax (mOD/min) of the turbidity was calculated. Using the Vmax of a similar mixture containing the coaggregation buffer instead of the test substance as control (100%), the percent coaggregation was calculated. Based on a value thus obtained, the coaggregation reaction was measured.

(4) Results

The percent coaggregation was 16% for mannitol, 71% for palatinit, 35% for erythritol, 20% for xylitol, 62% for sorbitol and 0% for lactitol. Thus, these substances exhibited an effect for inhibiting the coaggregation of cariogenic bacteria and bacteria of the genus *Fusobacterium*.

Example 3

Plaque was collected and various coaggregation inhibitors were applied thereto. Based on a pH change of the plaque measured after that, it was judged whether an acid was generated due to the decomposition of these inhibitors in the oral cavity. Described specifically, after termination of all the oral cleaning habits such as tooth brushing for one week, plaque attached to the tooth surface was collected physically by using a dental scaler. Just after collection, the plaque was diluted into 5 wt. % with physiological saline and dispersed therein, whereby a plaque suspension was prepared. To 0.5 mL of the resulting plaque suspension was added each coaggregation inhibitor to give a concentration of 0.9% (wt/vol %). After adjustment of its pH to 7 with dilute hydrochloric acid or dilute sodium hydroxide solution, variations in pH at 37° C. were traced. The pH was measured using a pH meter "TWIN-B212", product of Horiba, Ltd.

As a result, a pH decrease was observed from the plaque suspensions to which lactose, galactose and galactose monolaurate were added, respectively, suggesting that they were each decomposed to generate an acid. On the other hand, almost no pH change was observed in the plaque suspensions to which the compounds represented by the formulas (A) and (C), that is, β-octyl galactoside and α,β-lauryl galactoside had been added, respectively, suggesting that they were not decomposed in the mouth by the oral bacteria and did not generate an acid.

Example 4

Oral pastas shown in Table 2 were prepared and the resulting dentifrices were evaluated for their effect for reducing cariogenic bacteria in the plaque. Described specifically, three male volunteers in their thirties who had no carious pit and had a ratio of cariogenic bacteria of from 0.2 to 0.5% were asked to clean their teeth with 1 g of the oral pasta three times a day and a change in the ratio of cariogenic bacteria in their plaque was assayed one month after the cleaning was started. The ratio of cariogenic bacteria in the plaque was measured as follows. The saliva was collected from them while asking them to chew a plaque-rifling gum (provided of BML) for 5 minutes after the tooth cleaning was terminated for 12 hours. The saliva sample thus collected contained the plaque separated from the tooth surface. The ratio of the cariogenic bacteria was determined by calculating a ratio of the cariogenic bacteria count to the total streptococci count in the thus-collected saliva. The cariogenic bacteria count was determined by diluting the thus-collected saliva 100-fold with 0.1M phosphate buffered saline (PBS) having pH 7.4 and smearing 50 μL of it to an improved MSB agar medium (JP-A-2002-027975) by using a spiral plater (product of IUL Instruments). The total streptococci count was determined by diluting the thus collected saliva 10000-fold with PBS and smearing it to an MS agar medium (product of Japan Becton, Dickinson and Company) in a similar manner. The agar media to which respective bacteria had been smeared were subjected to anaerobic cultivation at 37° C. for 48 hours by using an AnaeroPack anaerobic cultivation system (product of Mitsubishi Gas Chemical). After cultivation, the number of colonies in a proper region was counted and a ratio of the cariogenic bacteria count to the total streptococci count was calculated.

TABLE 2

| Raw materials (mass %) | Example 4 | Comp. Ex. 1 | Comp. Ex. 2 |
| --- | --- | --- | --- |
| α,β-Lauryl galactoside | 5 | | |
| β-Lauryl glucoside | | 5 | |
| Sodium lauryl sulfate | | | 2 |
| Hydroxyethyl cellulose | 2.5 | 2.5 | 2.5 |
| Spearmint oil | 0.3 | 0.3 | 0.3 |
| Peppermint oil | 0.2 | 0.2 | 0.2 |
| Saccharin sodium | 0.2 | 0.2 | 0.2 |
| Red No. 106 | 0.0002 | 0.0002 | 0.0002 |
| Purified water | Balance | Balance | Balance |

Figure 2:
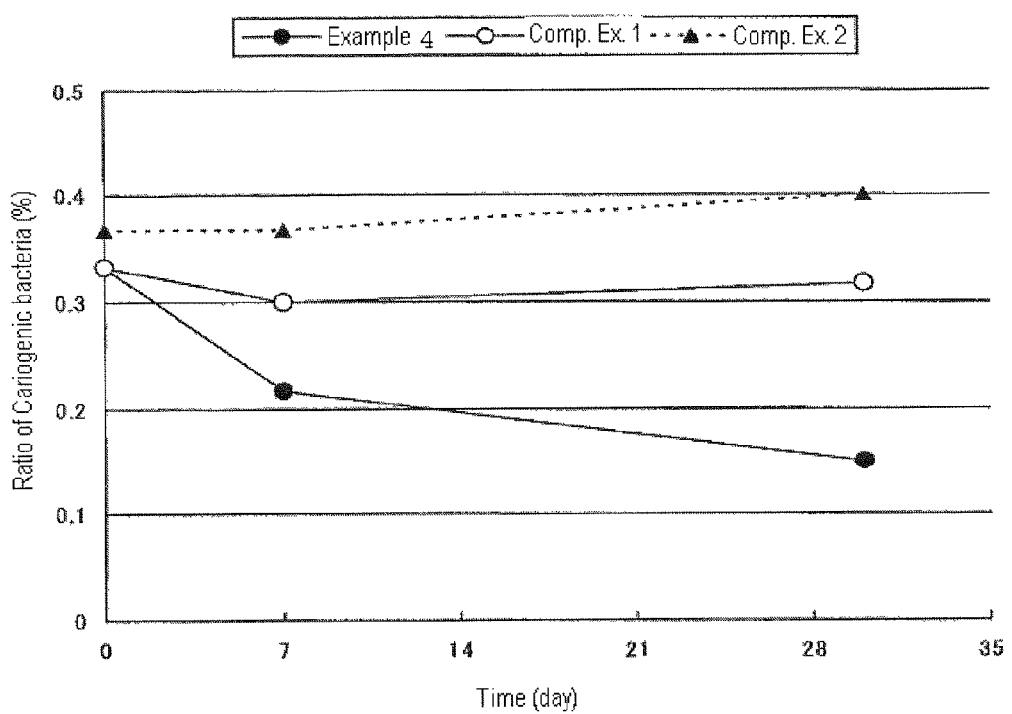
FIG. 2 illustrates a ratio of cariogenic bacteria contained in the plaque.

As a result illustrated in FIG. 2, the oral pasta containing lauryl glucoside and oral pasta containing sodium lauryl sulfate, each of Comparative Example, did not reduce the cariogenic bacteria ratio in the plaque, while the oral pasta containing α,β-lauryl galactoside of Example 5 caused a marked decrease in the cariogenic bacteria ratio in the plaque.

Example 5

A dental paste of the present invention having the following formulation was prepared.

| | |
|---|---|
| Sorbitol | 35 mass % |
| Silicic anhydride | 20 mass % |
| Concentrated glycerin | 5 mass % |
| α,β-Lauryl galactoside | 5 mass % |
| Carboxymethylcellulose sodium | 1 mass % |
| Flavor for dentifrice | 1 mass % |
| Sodium fluoride | 0.2 mass % |
| Saccharin sodium | 0.2 mass % |
| Purified water | Balance |
| Total | 100 mass % |

Example 6

A dental paste of the present invention having the following formulation was prepared.

| | |
|---|---|
| Sorbitol | 28 mass % |
| Silicic anhydride | 20 mass % |
| Concentrated glycerin | 8 mass % |
| Erythritol | 5 mass % |
| Sodium lauryl sulfate | 1.2 mass % |
| Carboxymethylcellulose sodium | 1 mass % |
| Flavor for dentifrice | 1 mass % |
| α,β-Lauryl galactoside | 0.5 mass % |
| Sodium fluoride | 0.2 mass % |
| Saccharin sodium | 0.2 mass % |
| Purified water | Balance |
| Total | 100 mass % |

Example 7

A mouth wash of the present invention having the following formulation was prepared.

| | |
|---|---|
| Ethanol | 15 mass % |
| Xylitol | 7 mass % |
| Polyoxyethylene hydrogenated castor oil | 2 mass % |
| Saccharin sodium | 0.5 mass % |
| β-Octyl galactoside | 0.2 mass % |
| Flavor for mouth wash | 0.2 mass % |
| Sodium benzoate | 0.1 mass % |
| Purified water | Balance |
| Total | 100 mass % |

What is claimed is:

1. A method for inhibiting coaggregation between bacteria of the genus *Fusobacterium* and cariogenic bacteria in the oral cavity, said method comprising
    (a) applying, into said oral cavity, a paste or liquid composition that comprises an effective amount of a compound represented by the following formula (A):

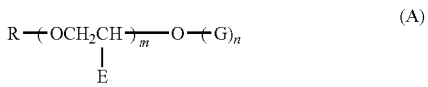

wherein, R represents a substituted or unsubstituted, linear or branched alkyl group having from 8 to 14 carbon atoms, G represents a galactose residue, E represents a hydrogen atom or a methyl group, m stands for an integer of from 0 to 200, and n stands for an integer of from 1 to 30, and
    (b) inhibiting said coaggregation of said bacteria of the genus *Fusobacterium* with said cariogenic bacteria in said oral cavity and decreasing the ratio of the cariogenic bacteria count to the total streptococci count in plaque in said oral cavity as a result of said applying.

2. The method of claim 1, wherein E is said hydrogen atom.

3. The method of claim 1, wherein m is 0-3.

4. The method of claim 1, wherein n is 1-3.

5. The method of claim 1, wherein R in formula (A) is selected from the group consisting of n-octyl, n-decyl, and n-dodecyl.

6. The method according to claim 1 or claim 2, wherein R represents a lauryl group.

7. The method according to claim 1 or claim 2, wherein said m=0.

8. The method of claim 1, wherein said composition also comprises a surfactant that is other than the compound represented by formula (A).

9. The method of claim 1, wherein said composition also comprises ethanol.

10. A method for inhibiting coaggregation between bacteria of the genus *Fusobacterium* and cariogenic bacteria, in the oral cavity, said method comprising
    (a) applying, into said oral cavity, a paste or liquid composition that comprises an effective amount of a mixture of two or more compounds represented by the following formula (C):

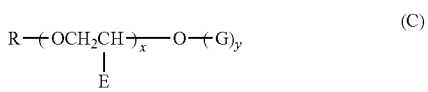

wherein, R represents a substituted or unsubstituted, linear or branched alkyl group having from 8 to 14 carbon atoms on average, G represents a galactose residue, E represents a hydrogen atom or a methyl group, x stands for the number of from 0 to 200 and y stands for the number of from 1 to 30, and
    (b) inhibiting said coaggregation of said bacteria of the genus *Fusobacterium* with said cariogenic bacteria in said oral cavity and decreasing the ratio of the cariogenic bacteria count to the total streptococci count in plaque in said oral cavity as a result of said applying.

11. The method of claim 10, wherein x is 0-3.

12. The method of claim 10, wherein y is 1-3.

13. The method according to claim 10, wherein said x=0.

14. The method of claim 10, wherein said composition also comprises a surfactant that is other than the compound represented by formula (C).

15. The method of claim 10, wherein said composition also comprises ethanol.

16. The method according to any one of claims 1 to 10, wherein said composition further comprises a sugar alcohol having from 4 to 12 carbon atoms.

17. The method according to claim 16, wherein said sugar alcohol is selected from the group consisting of sorbitol, mannitol, xylitol, erythritol, palatinit and lactitol.

18. The method according to any one of claims 1 to 10, wherein said composition is a paste composition.

19. The method according to any one of claims 1 to 10, wherein said composition is a liquid composition.

20. The method of claim 1 or claim 10, wherein the cariogenic bacteria comprise *Streptococcus mutans* or *Streptococcus sobrinus*.

* * * * *

UNITED STATES PATENT AND TRADEMARK OFFICE
CERTIFICATE OF CORRECTION

| | | |
|---|---|---|
| PATENT NO. | : 8,834,852 B2 | Page 1 of 1 |
| APPLICATION NO. | : 12/772492 | |
| DATED | : September 16, 2014 | |
| INVENTOR(S) | : Itano et al. | |

It is certified that error appears in the above-identified patent and that said Letters Patent is hereby corrected as shown below:

In the Claims

Column 10, line 65
Please replace "claims 1 to 10" with --claims 1, 2 and 10--

Column 11, line 4
Please replace "claims 1 to 10" with --claims 1, 2 and 10--

Column 11, line 6
Please replace "claims 1 to 10" with --claims 1, 2 and 10--

Signed and Sealed this
Fourteenth Day of April, 2015

Michelle K. Lee
*Director of the United States Patent and Trademark Office*